United States Patent [19]

DeVries et al.

[11] Patent Number: 5,540,946

[45] Date of Patent: Jul. 30, 1996

[54] METHOD OF APPLYING PRIMERS ONTO GLASS ELEMENT OF VEHICLES

[75] Inventors: James E. DeVries, North Olmsted; Kamal Kumar, Lorain, both of Ohio

[73] Assignee: Nordson Corporation, Westlake, Ohio

[21] Appl. No.: 359,711

[22] Filed: Dec. 20, 1994

Related U.S. Application Data

[63] Continuation of Ser. No. 979,126, Nov. 20, 1992, abandoned.

[51] Int. Cl.$^6$ ............................... B05D 1/00; B05D 5/00
[52] U.S. Cl. ................... 427/8; 427/10; 427/284; 427/289; 118/665; 118/668; 118/708; 356/372; 250/338.1; 250/342
[58] Field of Search ................... 427/8, 10, 163, 427/284, 287; 118/665, 708, 717, 668; 356/372; 250/560, 561

[56] References Cited

U.S. PATENT DOCUMENTS

| | | |
|---|---|---|
| 3,193,689 | 7/1965 | Kerr . |
| 3,370,633 | 5/1973 | Kennedy ........................ 250/222.1 |
| 3,899,663 | 8/1975 | Pirlet . |
| 4,217,053 | 8/1980 | Lavanchy et al. ............... 356/372 |
| 4,260,260 | 4/1981 | Letort et al. . |
| 4,306,812 | 12/1981 | Lapp et al. . |
| 4,330,354 | 5/1982 | Deubner et al. . |
| 4,416,541 | 11/1983 | Studer . |
| 4,498,901 | 2/1985 | Finch . |
| 4,532,723 | 8/1985 | Kellie et al. . |
| 4,662,540 | 5/1987 | Schroter . |
| 4,666,732 | 5/1987 | Schucker . |
| 4,820,281 | 4/1989 | Lawler . |
| 4,854,698 | 8/1989 | Schmidt . |
| 4,887,903 | 12/1989 | Frisco et al. ..................... 356/372 |
| 4,905,512 | 3/1990 | Hayashi . |
| 4,922,852 | 5/1990 | Price . |
| 4,935,261 | 6/1990 | Srivastava et al. . |
| 4,963,757 | 10/1960 | Liefde et al. . |
| 5,015,867 | 5/1991 | Siegel et al. . |
| 5,026,989 | 6/1991 | Merkel ........................... 250/338.1 |
| 5,054,650 | 9/1991 | Price ................................... 222/1 |
| 5,086,640 | 2/1992 | Nagata et al. . |
| 5,088,827 | 2/1992 | Kyriakis . |
| 5,125,744 | 6/1992 | Watanabe . |
| 5,133,521 | 7/1992 | Gutauskas . |
| 5,144,151 | 10/1992 | Thorne et al. ...................... 250/571 |
| 5,182,938 | 2/1993 | Merkel . |
| 5,208,064 | 5/1993 | Becker et al. ......................... 427/8 |
| 5,277,927 | 1/1994 | Burns et al. .......................... 427/8 |
| 5,322,706 | 6/1994 | Merkel et al. . |
| 5,370,905 | 12/1994 | Varga et al. ........................ 427/168 |

FOREIGN PATENT DOCUMENTS

| | | |
|---|---|---|
| 0379908 | 8/1990 | European Pat. Off. . |
| 0163069 | 1/1991 | European Pat. Off. . |
| 9110924 | 10/1991 | Germany . |

OTHER PUBLICATIONS

Int. J. Computer Integrated Manufacturing, 1991, vol. 4, No. 5, pp. 315–320 On–Line Control of a Manufacturing Cell Using Visual Inspection, Razban & Davis.

LX2series Laser Through–beam Photoelectric Sensor (2 pages).

SAE International—Photo Sensor for Glass Primer Application When Bonding Windshield Shinji Okuda & Tsuyoshi Nagata (authors) Feb. 25–Mar. 1, 1991 (cover page & pp. 1–8).

LX2series Laser Through–beam Photoelectric Sensor (2 pages), Sep. 1991.

Int. J. Computer Integrated Manufacturing, 1991, vol. 4, No. 5, pp. 315–320 *On–line Control of a Manufacturing Cell Using Visual Inspection*, A. Razban & B. L. Davis.

Nordson Corporation, *Airless Spray Coatings Application*, Eric Nord (4 pages); Reprinted from Materials Protection, Mar. 1964.

Nordson Hot Melt Spray Guns; Nov. 1990.

Meltex™ Hot Melt Coater CT 5000; Nordson Corporation, 1991.

Meltex™ Hot Melt Coater CT 6000; Nordson Corporation, 1991.

Meltex™ Hot Melt Coating Head BC 40; Nordson Corporation, 1991.

H–200 Series Slot Nozzles; Nordson Corporation, Aug. 1989.

Flexible Solutions For Label Producers; Nordson Corporation, Sep. 1991.
The Select Coat® System; Nordson Corporation, 1990.
*New Technology for Conformal Coating Application*; Nordson Corporation; Reprinted from Hybrid Circuit Technology Magazine, Jul. 1989.
Powder Coating Systems; Nordson Corporation, Sep. 1991.

*Primary Examiner*—Shrive Beck
*Assistant Examiner*—Brian K. Talbot
*Attorney, Agent, or Firm*—Raymond J. Slattery, III

[57] ABSTRACT

A dispensed bead (10) of material is disposed between a sensor pair (14) for monitoring the bead. The sensor pair (14) transmits a beam of light towards the bead of material. A signal is generated which corresponded to the amount of light received. By utilizing this signal, gaps or other discontinuities can be found. This signal can also be used to determine the height of the bead and generate a profile thereof. The signal can be used in a closed loop feedback control system to control the amount of material dispensed from the dispenser.

7 Claims, 3 Drawing Sheets

METHOD OF APPLYING PRIMERS ONTO GLASS ELEMENT OF VEHICLES

This application is a continuation of Ser. No. 07/979,126, filed Nov. 20, 1992, now abandoned.

BACKGROUND OF THE INVENTION

This invention relates generally to the dispensing of fluid materials onto substrates. More particularly, the invention relates to the detection and/or monitoring of a bead of material which has been deposited onto a substrate. Specifically, this invention is applicable for the detection of the presence of voids, gaps, and other discontinuities associated with a deposited bead of material, such as, for example, a bead of an adhesive, sealant, or caulk, as well as determining other qualities of the bead, such as its height; cross-section or the amount of material dispensed therein. This invention is especially useful in the monitoring of a bead of material dispensed onto the periphery of window glass, such as a windshield or other glass element, for an automobile or other vehicles, in preparation of adhesively bonding the glass to the body flange of the vehicle.

The presence of an air bubble passing through a nozzle of a dispensing system or a reduction in the material supply pressure may cause a discontinuity in the bead deposited upon the substrate. If the air bubble or the reduction in the material supply pressure is small, the effect on the resulting bead may be minimal. However, if the air bubble is large or the material supply pressure is insufficient, the effect may produce a significant discontinuity in the bead or a bead having an insufficient cross-section. In some applications, discontinuities in the bead may not be critical, however, in others they may be. For example, discontinuities in a bead of the adhesive/sealant applied to a windshield may not only affect its ability to act as a moisture barrier, but it also may affect the strength of the bond of the windshield to the vehicle.

Attempts have been made to detect gaps in the dispensed bead automatically as opposed to an operator's visual inspection. For example, U.S. Pat. No. 4,662,540 to Schroter illustrates one attempt to detect the presence of air bubbles in sealants, mastics, and adhesives. In this system, a pressure transducer produces an electrical signal which corresponds to the instantaneous pressure of the fluid. This electrical signal is then differentially amplified and compared to a threshold. U.S. Pat. No. 5,086,640 to Nagata, et al. illustrates another attempt to detect a breakage or other discontinuity in the bead by monitoring the vibration of the dispenser. Both of these patents attempt to detect a discontinuity in the bead before the bead is actually deposited onto the substrate. Neither of these two patents actually monitor the bead after it has been deposited onto the substrate. Rather, they infer that a discontinuity has occurred as opposed to actually verifying that a discontinuity has actually occurred.

Although not in the assembly of automobile glass, attempts have been made to monitor a bead of material after it has been dispensed onto a substrate. For example, U.S. Pat. No. 5,026,989 monitors energy radiating from material dispensed onto a substrate utilizing an infrared sensor. However, this device must be used with a heated adhesive, such as a hot melt adhesive. It therefore would not be useful with room temperature adhesives. German Utility Patent G 91 10 924.8 illustrates directing a beam of light onto a substrate before the adhesive is applied and directing the beam of light onto the substrate after the drop of adhesive has been applied. This device monitors whether or not a drop of adhesive has been applied to a substrate as opposed to monitoring the complete bead of material. This device requires a reflective substrate, such as metal and may not be suitable for glass.

While gaps or complete breakages of the bead are undesirable, other defects of the bead may also affect its performance. For example, voids in the extruded bead, such as through holes, may also affect the ability of the bead to act as a moisture barrier and/or affect the strength of the bond of the window glass to the vehicle. Similarly, beads that are continuous, but not of a sufficient height or cross-section, may also be undesirable. In like manner, beads exceeding a certain height may also be undesirable. Therefore, it is desirable to be able to determine not only discontinuities in the bead, but also to detect voids and those beads not falling within certain limits. Up until now, this has not been possible.

SUMMARY OF THE INVENTION

It is therefore among the objects of this invention to provide for the detection of gaps or discontinuities in a dispensed bead on a substrate.

It is also an object of one embodiment of this invention to provide for the monitoring of a bead dispensed upon a substrate to detect voids within the bead and to detect beads not having a desirable bead height and/or cross-section.

It is also an object of this invention, according to one embodiment, to provide for the monitoring of a dispensed bead and to adjust the amount of material dispensed from a dispenser as a result of said monitoring.

These and other objects of the invention may be accomplished by:

(a) interposing the dispensed bead of material between a sensor pair, said sensor pair including a transmitting means and a receiving means diametrically opposed to said transmitting means, and causing relative movement between said sensor pair and said bead; (b) transmitting a beam of light; (c) detecting the amount of light received by the receiving means; (d) generating a signal correlated to the amount of light detected; and (e) in response to said signal, performing at least one of the following steps: (i) determining the height of said bead; (ii) comparing said signal to a reference signal.

These and other objects of the invention may also be accomplished by:

(a) dispensing a bead of material from a dispenser onto a substrate; (b) interposing the dispensed bead between a sensor pair, said sensor pair including a transmitting means and a receiving means diametrically opposed to said transmitting means; (c) causing relative movement between said sensor pair and said bead while transmitting a beam of light; (d) detecting the amount of light received by the receiving means; (e) generating a signal correlated to the amount of light detected; and (f) in response to said signal, performing at least one of the following steps: (i) determining the height of said bead; (ii) determining the amount of material dispensed; (iii) determining defects in the deposited bead; (iv) comparing said signal to a reference, generating a correction factor correlated to the difference between said signal and said reference, utilizing the correction factor to generate a control signal, and utilizing said control signal to adjust the amount of material dispensed from said dispenser.

DESCRIPTION OF THE DRAWINGS

The following is a brief description of the drawings in which like parts may bear like reference numerals and in which.

DETAILED DESCRIPTION OF THE INVENTION

Figure 1:
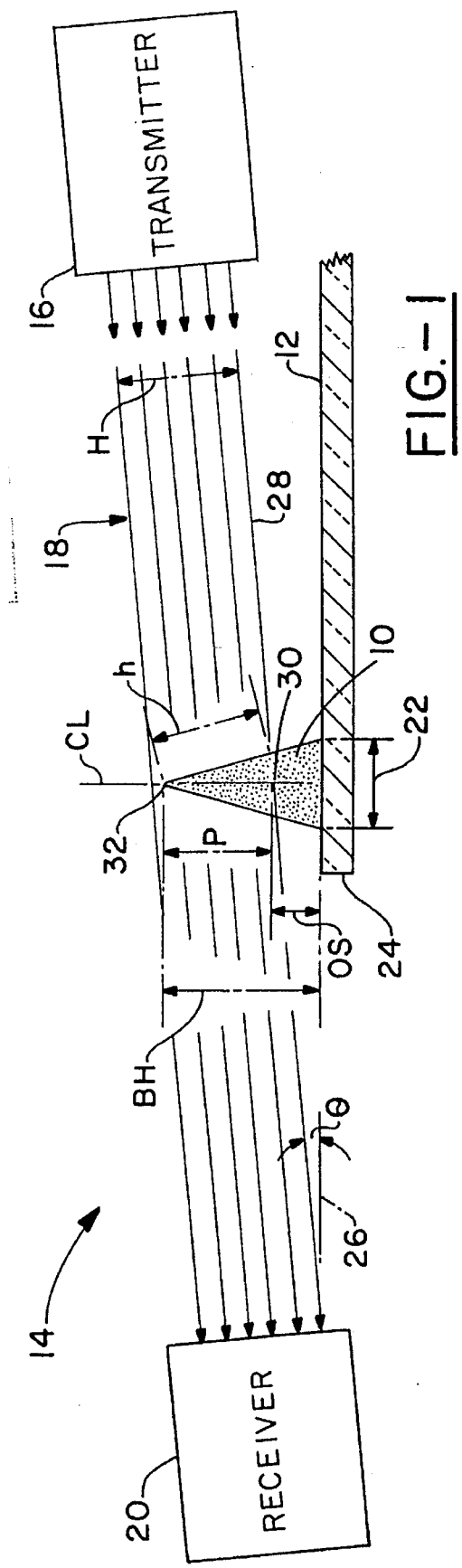
FIG. 1 is a schematic representation of a cross-sectional view of a substrate, such as window glass for vehicles, having peripheral bead of material deposited thereon and a sensor pair according to one embodiment of the invention.

With reference to FIG. 1, there is illustrated a bead of material 10, which may be for example an adhesive, sealant, or caulk, dispensed onto a substrate 12. In one particular application, the substrate 12 may be window glass for a vehicle, while the bead of material 10 may be an adhesive, such as illustrated in EP 379 908 assigned to Essex Specialty Products, Inc., which is used in the assembly of automobile window glass. While the illustrated bead of material has a triangular cross-sectional area, this invention is not limited to such cross-sections, but will work with other bead shapes such as, for example, rectangular cross-sections.

The dispensed bead of material 10 is interposed between the sensor pair, shown generally as reference numeral 14. The sensor pair includes the transmitter 16 for transmitting a beam of light 18 comprising a plurality of collimated rays of light. The transmitter may include for example a semiconductor laser which transmits a beam of light to a projecting lens unit. The projecting lens unit aligns the rays of light so that they are transmitted in a parallel relationship to one another from the transmitter 16. The receiver 20 receives the beam of light and generates a signal, such as a voltage output, in relationship to the quantity of light received. The sensor pair 14 could be, for example, a laser through beam photoelectric sensor, or other such photoelectric sensor. Also, the source of light does not necessarily have to be a laser, however, it is important that the rays of light transmitted from the transmitter are collimated.

The cross-sectional area (the area perpendicular to the axis of transmission) of the beam of light 18, transmitted from the transmitter 16, may vary depending upon the size of the deposited bead to be detected. For example, in an automotive windshield application, in which a bead of urethane was deposited about the periphery thereof, and having a bead height BH of about 14 mm, it was found that a beam of light transmitted from the transmitter having a Height H of 10 mm and a Width of 1 mm was sufficient.

The signal generated by the receiver 20 is proportionate to the amount of light received. The more light received by the receiver, the larger the output signal. Conversely, the less light received by the receiver, the lower the output signal. In other words, beads of material having a larger bead height BH will generate a lower output signal due to the fact that more light is blocked from reaching the receiver. Beads of a lower bead height BH will allow more light to pass to the receiver and thereby generating a larger output signal. If for some reason the bead is not present at all, all of the light should then pass to the receiver producing the largest output signal therefrom. By monitoring the output signal from the receiver, the presence or absence of the bead can be detected as well as its height which in some instances, will allow the volume or cross-sectional area to be determined.

Relative movement between the sensor pair 14 and the bead 10 allows the sensor pair to scan along the length of the bead of material 10. With such movement, it is preferred that a constant elevation is maintained above the substrate, so as to have a constant reference point. In particular, the constant reference or elevational distance should be in reference to that area 22 of the substrate 12 in which the base of the bead contacts the substrate. While the above invention may be used separately from a dispenser to monitor the bead, it is believed to be preferred that the sensor pair be mounted in a fixed relationship to the dispensing nozzle. If the nozzle dispenses directly onto the substrate, then the sensor pair will be maintained at a constant elevation above the substrate as the bead is deposited thereon. This will simplify the bead height measurement because the offset will be constant and will not have to be separately determined and/or maintained by, for example, proximity sensors.

Also, mounting the sensor pair 14 in a fixed relationship to the dispensing nozzle helps to eliminate alignment problems in relationship to the position in which the bead of material is deposited onto the substrate. For example, with reference to FIG. 1, the bead of material 10 could be deposited on the substrate 12 such that it is closer to or farther away from the edge 24 of the substrate. This possible shifting of the position of the bead of material could then affect the accuracy of the bead height calculation. However, by having the sensor pair 14 carried by the nozzle and/or its associated dispenser, the distance between the dispense bead and the receiver or transmitter should be maintained.

Furthermore, by mounting the sensor pair in a fixed relationship to, and in close proximity to the dispensing nozzle allows for real time monitoring of the bead which can then be used to control the dispensing of the bead as will be discussed further below.

The sensor pair 14 may be oriented at an angle $\Theta$ with respect to the substrate 10. The angle $\Theta$ is the angle formed between the intersection of a line 26 parallel to the area 22 of the substrate in which the base of the bead contacts the substrate and a line parallel to the transmission of the bead of light. Angling the sensor pair in this fashion has several advantages. First, this allows for detecting or scanning a bead of material when more than one bead of material has been deposited onto the substrate. This will be discussed further below. Another advantage is that it allows the sensor pair to monitor along the length of a bead of material which is not deposited in a straight line and/or avoid obstructions. For example, in applying a bead of adhesive about the periphery of a piece of automobile window glass, the bead of material must be applied in the corner regions. Depending upon the tightness of the corner and the angular change in direction, the sensor pair could contact the bead of material as it sweeps through the curvature of the corner. This contacting of the sensor pair with the bead could damage the bead, and therefore the integrity of the seal, as well as contaminating the sensor pair with adhesive. Neither of these occurrences are desirable. Angling the sensor pair, however, allows the transmitter 16 to pass over and not contact the dispensed bead 12 while passing through a curved portion of the dispensed bead. Also, angling the sensor pair allows the sensor pair to pass over obstructions which may be present on the substrate. For example, in the assembly of automotive window glass, the sensor pair may have to avoid the rearview mirror or electrical studs or other connections. Furthermore, by angling the sensor pair, the horizontal distance between the sensor pairs may be reduced thereby simplifying the mounting requirements and reducing errors in the transmission of light due to the angular torque applied to each sensor pair.

It is to be noted that the position of the transmitter 16 and receiver 20 may be reversed without departing from the spirit and scope of the invention, such that the receiver is located above the substrate 10 as opposed to the transmitter 16.

In that in most cases, a certain minimum amount of material must be deposited on the substrate, it is not necessary to determine that a complete absence of material being deposited on the substrate has occurred. Bearing this in mind, the receiver and transmitter may be oriented in a position to determine when the bead height is less than this minimum threshold. For example, the center of the beam could be oriented such that it will intersect the apex 32 of the bead. This will result in half of the beam being above and the other half being below the apex 32. If the acceptable height at which a bead can vary is less than half of the beam height H, then beads falling outside this tolerance can be detected. The portion 28 of the beam of light 18 closest to the substrate 10 which intersects the centerline of the bead of material at point 30 will then be a known distance above the substrate 10. The distance between the substrate and the intersection point 30 is the offset OS. The distance along the centerline from point 30 to the apex 32 of the bead 10 is the distance P. The bead height BH is therefore the distance P+OS. P can be determined from the following equation:

$$P = \frac{h}{\arc \cos \Theta}$$

where h is the distance from the apex 32 of the bead of material to the portion 28 of the beam of light 18 closest to the substrate 12 taken along a line perpendicular to the transmission of light. For a given angular orientation Θ and a constant offset OS, the only remaining variable therefore is h. However, h corresponds to the amount of light that is not received, i.e. blocked by the bead of material, by the receiver 20. Therefore, the signal generated by the receiver 20 will be directly proportional to h.

Figure 2:
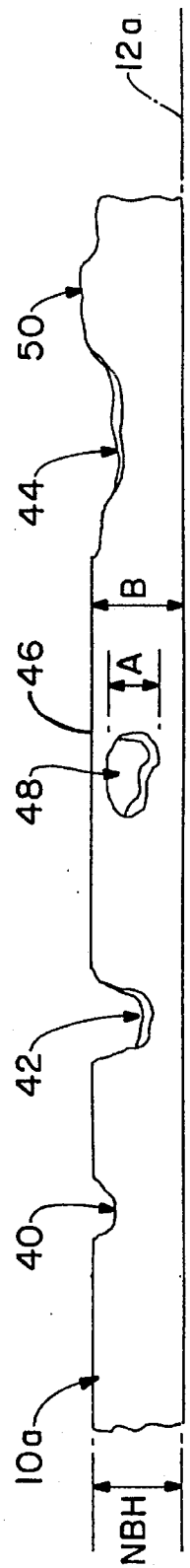
FIG. 2 is an elevational view of a portion of the profile of the bead deposited on a substrate.

Now with reference to FIG. 2, there is illustrated an elevational view of a portion of a bead 10a deposited onto a substrate. FIG. 2 illustrates several different types of defects which may be present in a dispensed bead of material. For example, the bead may not be completely formed, leaving voids or gaps 40, 42, 44 along the outer edge 46 of the bead 10a. As used herein outer means the direction away from the substrate 12a. Another type of defect that could be present would be a hole 48 which is entrained in the dispensed bead. These types of defects typically result from a disruption of flow of material from the dispenser. This may result, for example, from air bubbles trapped within the dispensing material, or an inadequate dispensing flow rate.

Another type of defect may result if much more material is dispensed than is normally required. This may result in the height of the bead being greater than normal, such as illustrated at 50. Too much adhesive may result in the excess adhesive being squeezed out when the substrate is bonded to another substrate.

Figure 3:
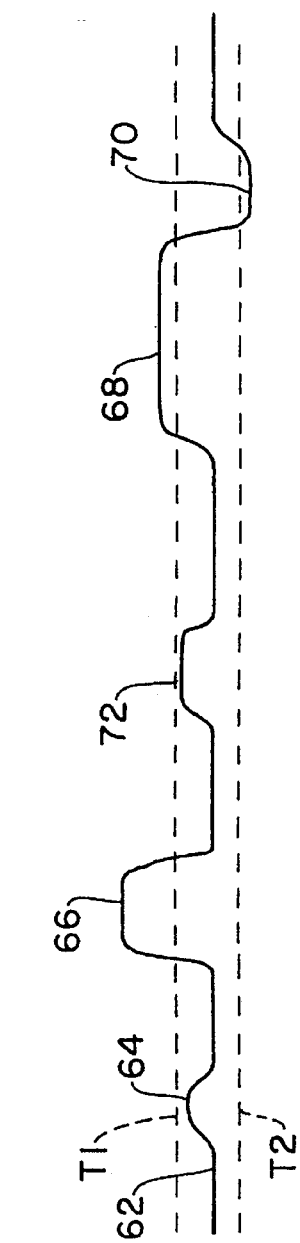
FIGS. 3 illustrates a signal generated in response to the bead of material deposited in FIG. 2.

As the sensor pair moves along the length of the bead, it will scan the bead and produce an output signal proportional to the height of the bead less the offset difference as described above. Now further with reference to FIG. 3, there is illustrated a signal generated by the receiver of the sensor pair corresponding to the bead profile of FIG. 2. As stated above, the signal that is generated increases as more light is received by the receiver. In this manner, the signal 62 increases from its normal level at 64, 66, and 68 which corresponds to the gaps 40, 42, and 44 respectively of the bead 10a. The greater the amplitude of the signal 62, the less the amount of material present in the bead, therefore signalling the greater gap. On the other hand, the amplitude of the signal will be reduced if the outer edge of the bead is higher than normal. Therefore, the amplitude of the signal is reduced at 70 to correspond to the increase in the bead height at 50 of the bead 10a. Thus, a fairly accurate bead height profile may be generated for the dispensed bead of material.

A through hole 48 will be detected because light will be allowed to pass therethrough. This will then produce an increase 72 in the signal 62. At this point, the signal 62 does not actually give the true bead height of the bead of material in this section. The signal will correspond to a "perceived" bead height. In other words, while the actual bead height in the area of the hole may be at its normal level, the hole in the bead will cause the sensor to perceive a bead of a lower height. In other words, the signal generated will actually correspond to the height of the bead B in the region of the hole minus the height A of the hole. In other words, as far as the receiver is concerned the hole 48 could just as easily be a gap similar to 40, 42, and 44. In most applications this will not be of concern because if the hole is of a sufficient size such that the signal exceeds a threshold level, the integrity of the bead most likely has been compromised and therefore should be noted as a defect. If, however, it is important to differentiate between holes and gaps similar to 40, 42 and 44, a scanning array transmitter may be used in which parallel rays of light are transmitted at different heights and times.

Since the sensor pair is monitoring the profile of the bead, and looking for gaps and voids therein, this method of detection is immune to pressure disturbances in the dispensing fluid. For example, it is known that a bubble passing through the dispenser introduces pressure disturbances within the flow of material. However, it is also known that other conditions can produce pressure fluctuations within the fluid material which may make it difficult to discern if a bubble has actually passed. For example, particles are sometimes dispensed from the dispenser which can produce pressure disturbance similar to the bubble. These particles can be cured or partially cured material of the mixture or contaminates which will not normally affect the integrity of the dispensed bead. As such, unless these particles somehow affect the bead profile, they will not be detected, thereby producing false error signals which have been known to affect some pressure monitoring systems.

The signal generated by the sensor, can be used to generate a bead profile for each work cycle. In the case of window glass, this provides a means for automatically recording the profile of each window glass installed on an automobile. This eliminates having an individual manually measure the profile.

It may be desirable to indicate those gaps, holes, and other discontinuities below a certain minimum level while ignoring others. This can be accomplished by indicating when the signal exceeds a threshold level T1 while ignoring those signals below this level. Likewise, it may be desirable to indicate those instances where the bead height exceeds a certain height, such as indicated by the signal exceeding the threshold level T2. As such, signals exceeding these thresholds T1, T2 could then activate an alarm or other type of alarm indication. However, depending upon the specific application, it may be desirable to indicate those gaps or discontinuities which not only exceed the respective thresholds, but exceed those thresholds for a certain length of time. This would allow for the detection circuitry to filter out short duration error signals. The output of the receiver 20 may be coupled to a signal processing circuitry for noise filtering, amplification and the like, if required. The output signal from the signal processing circuitry is then coupled to one of the inputs of a pair of comparators. If signal processing circuitry is not required, then the output of the receiver 20 may be coupled to the inputs of the comparators. A signal corresponding to the threshold reference limit T1 (minimum bead height) is coupled to the first comparator, while a signal corresponding to the threshold limit T2 (maximum bead height) is coupled to the other input of the second comparator. The output of first comparator is coupled to timing circuitry. Timing circuitry may include edge detecting circuitry and a timer or counter so that once the first comparator changes state, the timer begins timing or the counter begins counting. A third comparator is coupled to the output of the timing circuitry at one input and coupled at its other input to a signal DI1 corresponding to the minimum interval or length of time for which the threshold reference must be exceeded in order to have an error or alarm condition. As the first comparator changes state, the timing circuity will begin timing. The output from the timing circuitry corresponds to the actual length of time during which the threshold reference T1 has been exceeded. If threshold reference T1 has been exceeded for a time longer than the duration interval DI1, then third comparator will be activated causing the output to activate a latch circuit. The output of the latch circuitry may be coupled to an alarm circuitry, a computer, etc. to indicate that a gap has been detected in the bead. Similarly, the output of second comparator may be coupled to timing circuitry (similar to the previous timing circuitry ) which is in turn coupled to a fourth comparator. One input of the fourth comparator is coupled to a signal DI2 corresponding to the duration interval corresponding to the minimum length of time for which the threshold level T2 must be exceeded. The output of the fourth comparator may then be coupled to a latch circuit which in turn has its output coupled to an alarm circuitry, a computer, etc. for further processing.

Alternately, depending upon the specific application, it may be desirable to monitor the rate of change of the bead height signal. This may be accomplished by differentially amplifying the signal from the receiver. The differentially amplified signal may then be compared to high or low threshold levels such that an alarm or other indication may be given when such thresholds have been exceeded. Furthermore, it again may be desirous to indicate only those instances when a threshold has been exceeded for a predetermined length of time. In such case, the differentially amplified signal may be utilized with circuitry similar to that described above As discussed above, it is believed to be beneficial to angularly orient the sensor pair with respect to the substrate in order to navigate through curves or corners and to avoid contact with obstructions. As such, the sensor pair could be oriented at an angle $\Theta$ equal to zero during straight line deposition of the bead to a substrate, and then raised to an angle greater than zero when there is a change in the direction of the bead path such as entering a corner or when an obstruction is encountered, so that the sensor pair does not come in contact with the dispensed bead or the obstruction. This adjustment can be accomplished in response to a signal received from the robot controller. For example, as the robot begins to enter a curve, a signal may be sent to actuate a servo motor to rotate the angular orientation of the sensor pair relative to the substrate.

The exact angular orientation $\Theta$ may vary depending upon the cross-sectional configuration of the bead, the distance of the bead from the peripheral edge of the substrate, the spacing between the sensor pair, and other physical objects located on the substrate. For example, it is believed that for most single bead applications for automobile window glass, angle $\Theta$ within the range from about 0° to about 20° should be sufficient. However, this range can be increased due to the presence of other physical objects on the substrate, such as another dispensed bead, a rearview mirror or electrical connectors. For example, it is not inconceivable that the angle of orientation may be in the 45° to 60° range when used to monitor two different beads.

Figure 4:
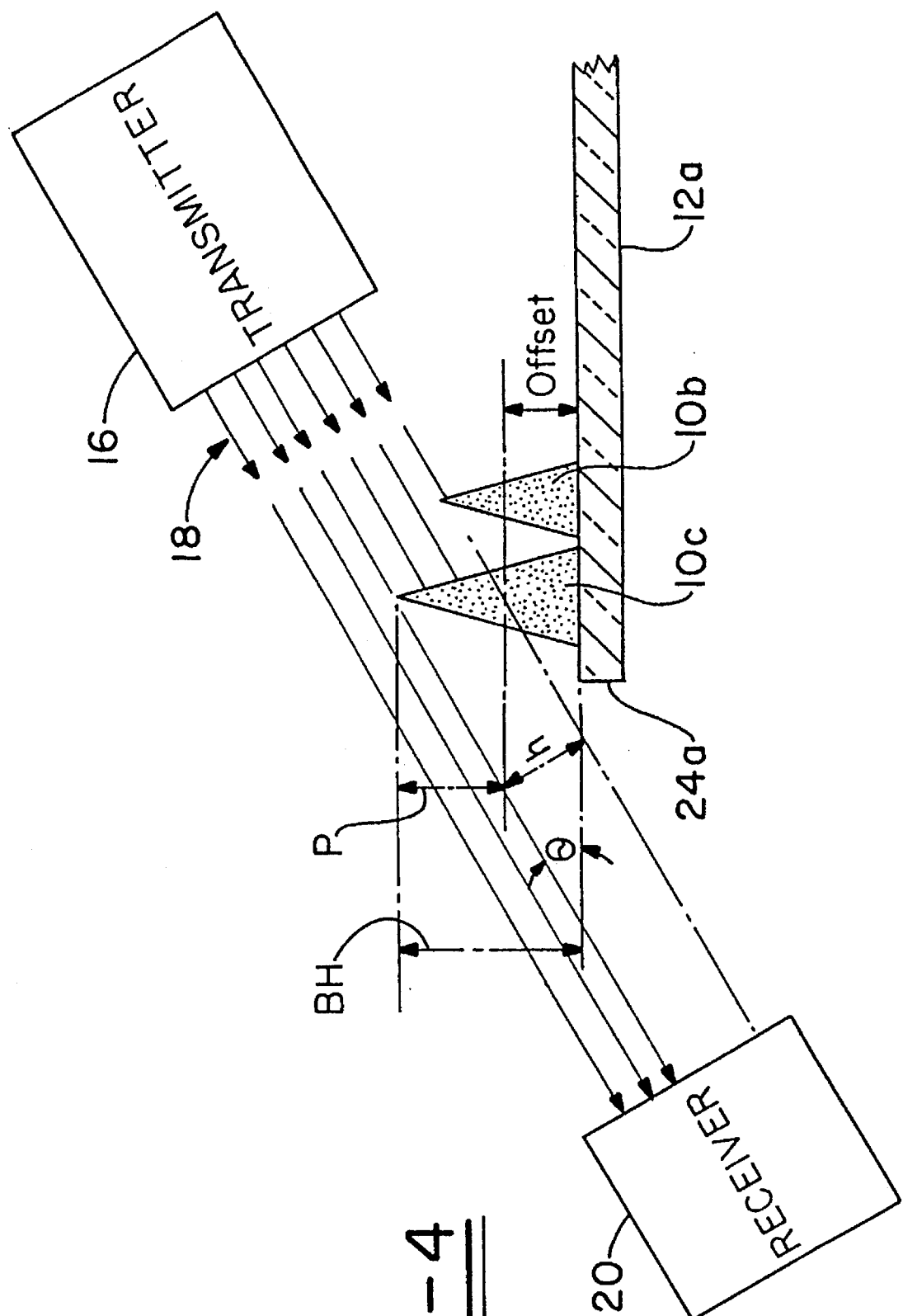
FIG. 4 is a schematic representation similar to that of FIG. 1, except for having two peripheral beads of material deposited onto the substrate.

With reference now to FIG. 4, there is illustrated a substrate 12a having two beads 10b, 10c dispensed thereon. In such a configuration, it may be necessary to monitor both beads. In such a case the bead farthest from the peripheral edge 24a of the substrate 12b would be dispensed and monitored. The second bead 10c located between the first bead 10b and the outer peripheral edge 24a of the substrate 12a would then be dispensed and monitored. In such a configuration, the angular orientation $\Theta$ of the sensor pair must be oriented such that the beam of light can adequately scan the second bead 10c without being blocked by the first bead 10b. In such a case, the angular orientation $\Theta$ will be dependent upon the height of the first dispensed bead 10b and the spacing between beads 10b,10c. Furthermore, the displacement of the first bead 10b from the peripheral edge 24a of the substrate may require that the sensor pair be first oriented at a first angle and then oriented at a second angle $\Theta$ in order to scan the second bead. In such a situation a servo motor may be required in order to rotate the sensor pair in order to change the angular orientation.

The signal generated by the receiver 20 may also be used as a feedback control signal for use in adjusting the amount of material dispensed onto a substrate. For example, the bead height signal generated from the receiver 20 may be compared to a desired bead height signal and as a result of such a comparison the amount of material being dispensed from the dispenser is either increased or decreased. If the bead height signal indicates that the actual bead height BH of the bead being deposited onto the substrate is less than the desired bead height, but greater than the minimum acceptable bead height, then the system may be adjusted in order to dispense more material from the dispenser. On the other hand, if it is found by such comparison that the actual bead height is greater than the desired bead height, but less than the threshold limit T2, then as a result of such comparison, the amount of material dispensed from the dispenser will be adjusted to produce a lower output.

Figure 5:
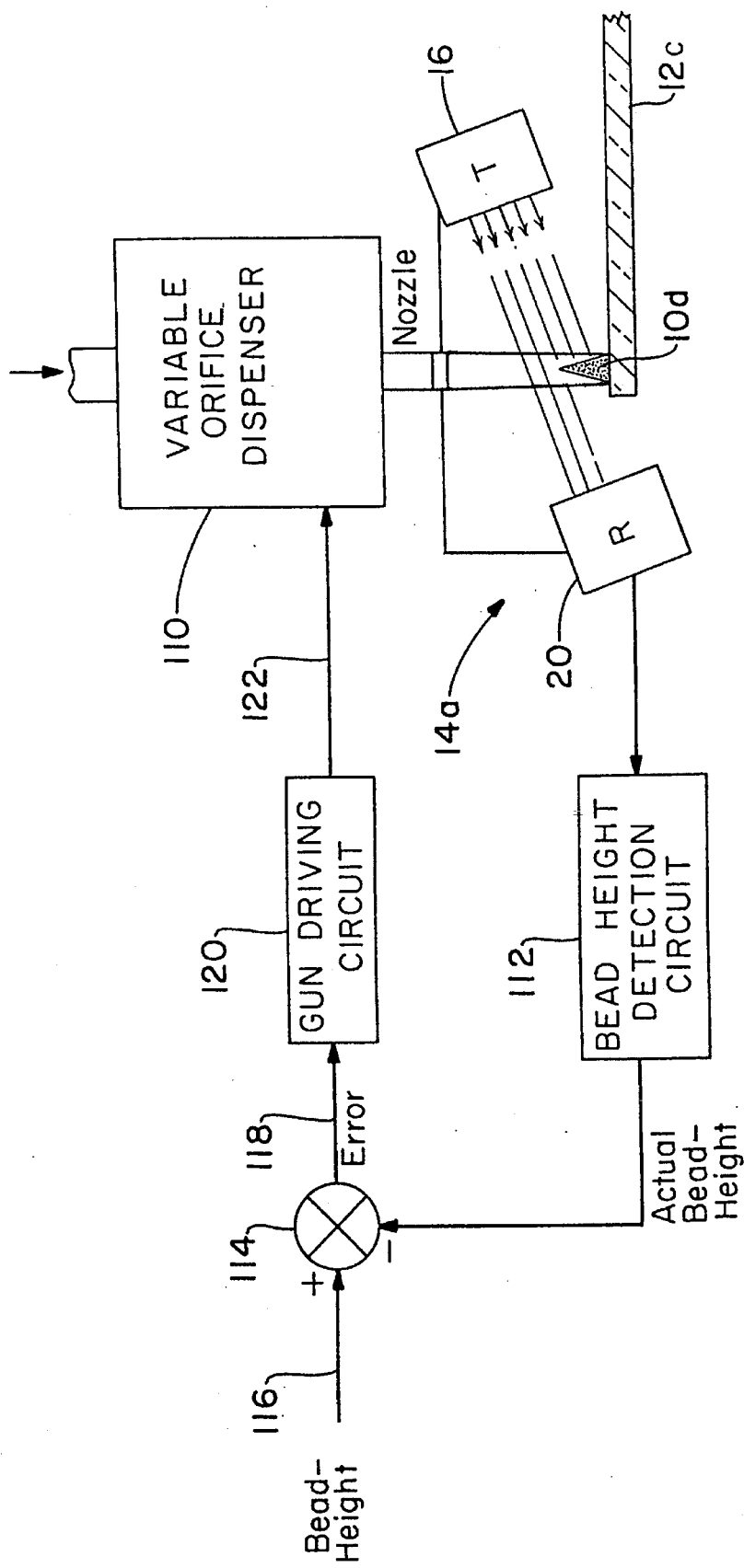
FIG. 5 is a schematic illustrating an aspect of the invention according to another embodiment of the invention.

For example, with reference to FIG. 5, there is illustrated a schematic diagram for controlling the amount of material being dispensed onto the substrate. A variable orifice dispenser 110 carries the sensor pair 14a as a bead of material 10d is dispensed therefrom onto a substrate 12c. The output of the receiver 20 is coupled to the bead height detection circuitry 112. The bead height circuitry 112 determines if any threshold limits have been exceeded and indicates any alarms as required. The detection circuitry also amplifies and/or scales the signal as required and can be outputed to the negative input of a summing junction 114. The desired bead height signal is coupled via line 116 to the positive input of the summing junction 114. The output of the summing junction 114 is coupled via line 118 to the gun driving circuitry 120 of the variable orifice dispenser 110. The gun driving circuitry 120 generates a gun driving signal which is coupled via line 122 to the variable orifice dispenser. A difference between the desired bead height and the actual bead height will be indicated as an error signal outputted from summing junction 114. The gun driving circuitry will provide a correction factor to adjust the gun driving signal in order to compensate for the error signal received from the summing junction 114. The correction factor can be determined from a look up table which takes into account the spread of movement. One type of variable orifice dispenser is the Nordson® Pro Flo® dispenser manufactured by Nordson Corporation, Westlake, Ohio. One embodiment of a Nordson Pro-Flo dispenser is illustrated in U.S. Pat. No. 5,054,650 the disclosure of which is hereby incorporated by reference.

In those applications in which the dispenser is not a variable orifice dispenser, but is rather an on/off dispenser, the error signal (which can be amplified and/or scaled) can generate a correction factor which, when coupled to a gear pump motor controller such that the error signal will produce appropriate changes in the rpm of the gear pump. The output of the gear pump is coupled to the dispenser so that the volumetric flow rate of the dispenser can be varied.

Furthermore, in those applications in which the cross-sectional area of the dispensed bead is substantially constant, the total amount of material dispensed during a work cycle may be determined and adjustments made in order to compensate for changes between work cycles. For example, the volume of the dispensed bead may be incrementally determined by the cross-sectional area for a given length of bead. If, for example, for a given tool speed and frequency response of the sensor, it is known that the bead height will be recorded every 0.5 mm (0.02 inches) along the length of the bead, then this incremental length may be multiplied by the respective cross-sectional area of the bead. For each cycle this volume may be totaled and compared to a respective reference. If from this comparison the amount of material is either over or under the desired amount, an adjustment may be made to vary the flow of material from the dispenser on the next subsequent piece in order to maintain desired volumetric output.

While certain representative embodiments and details have been shown for the purpose of illustrating the invention, it will be apparent to those skilled in the art that various changes and/or modifications may be made therein without departing from the spirit and scope of the invention. For example the signal illustrated in FIG. 3 could be adjusted to compensate for the offset distance. On such a case the signal would then correspond proportionally to the height of the bead. Also, the signal could be amplified, scaled, inverted, etc. as required.

It is claimed:

1. A method of depositing a bead of an adhesive, sealant, or caulk onto a vehicle window glass comprising the steps of:

(a) dispensing the bead of the adhesive, sealant, or caulk from a dispenser onto the vehicle window glass;

(b) interposing the dispensed bead between a sensor pair, said sensor pair including a transmitting means and a receiving means diametrically opposed to said transmitting means, and causing relative movement between said sensor pair and said bead;

(c) transmitting a beam of light, wherein the beam of light includes a plurality of parallel rays of light and wherein the beam of light is transmitted along a transmission angle, the transmission angle being an acute angle formed by a center line of the beam of light and a plane parallel to the glass upon which the bead is deposited such that the sensor pair will avoid contacting the bead, the glass, or other objects on the glass;

(d) detecting the amount of light received by the receiving means;

(e) generating a signal correlated to the amount of light detected; and (f) utilizing the signal to generate a bead height signal correlated to the height of the bead for indicating the height of the bead as well as for indicating an alarm for beads exceeding a high or low level threshold.

2. The method of claim 1 wherein the center line of the beam of light is oriented such that it will intersect with an apex of the bead.

3. The method of claim 2 wherein the bead height signal is determined by $$\frac{h}{\text{ARCCOS}\Theta} + OS$$

where h is the distance from the apex of the bead to a portion of the beam of light closest to the glass taken along a line perpendicular to the transmission of the beam of light, $\Theta$ is the transmission angle, and OS is a constant offset from the glass.

4. The method of claim 1 further including the step of determining a total volumetric output of the adhesive, sealant, or caulk dispensed during a work cycle; comparing the total output dispensed to a reference; and based upon the comparison, adjusting the control signal to adjust the flow of material from the dispenser during the next work cycle in order to maintain a desired volumetric output.

5. The method of claim 3 further comprising the step of changing the transmission angle to a different transmission angle during a work cycle.

6. The method of claim 1 further comprising the steps of:

dispensing another bead of an adhesive, sealant or caulk onto the glass, adjacent to the dispensed bead of step (a); and repeating steps (b) through (g) at a different transmission angle for said another bead of adhesive, sealant or caulk.

7. The method of claim 6 further comprising the steps of:

determining a total volumetric output of the adhesive, sealant, or caulk dispensed during a work cycle; comparing the total output dispensed to a reference; and based upon the comparison, adjusting the control signal to adjust the flow of material from the dispenser during the next work cycle in order to maintain a desired volumetric output.

\* \* \* \* \*